United States Patent
Sathiosatham et al.

(10) Patent No.: US 9,670,134 B2
(45) Date of Patent: Jun. 6, 2017

(54) SYNTHESIS OF (2-NITRO)ALKYL (METH)ACRYLATES VIA TRANSESTERIFICATION OF (METH)ACRYLATE ESTERS

(71) Applicant: ANGUS Chemical Company, Buffalo Grove, IL (US)

(72) Inventors: Muhunthan Sathiosatham, Chalfont, PA (US); Robert Wilczynski, Yardley, PA (US)

(73) Assignee: ANGUS CHEMICAL COMPANY, Buffalo Grove, IL (US)

( * ) Notice: Subject to any disclaimer, the term of this patent is extended or adjusted under 35 U.S.C. 154(b) by 0 days.

(21) Appl. No.: 14/780,446

(22) PCT Filed: Feb. 18, 2014

(86) PCT No.: PCT/US2014/016822
§ 371 (c)(1),
(2) Date: Sep. 25, 2015

(87) PCT Pub. No.: WO2014/158445
PCT Pub. Date: Oct. 2, 2014

(65) Prior Publication Data
US 2016/0046558 A1    Feb. 18, 2016

Related U.S. Application Data

(60) Provisional application No. 61/805,975, filed on Mar. 28, 2013.

(51) Int. Cl.
C07C 69/52 (2006.01)
C07C 201/12 (2006.01)
C07B 41/12 (2006.01)
C07B 43/02 (2006.01)

(52) U.S. Cl.
CPC ............ *C07C 201/12* (2013.01); *C07B 41/12* (2013.01); *C07B 43/02* (2013.01); *Y02P 20/582* (2015.11)

(58) Field of Classification Search
None
See application file for complete search history.

(56) References Cited

U.S. PATENT DOCUMENTS

| | | | |
|---|---|---|---|
| 2,388,844 A | 11/1945 | Hasche et al. | |
| 2,449,804 A | 9/1948 | D'Alelio et al. | |
| 5,183,930 A * | 2/1993 | Venter | C07C 67/03 560/217 |
| 5,210,199 A | 5/1993 | Grosius et al. | |
| 5,728,397 A | 3/1998 | Fuisz | |
| 7,071,351 B2 * | 7/2006 | Schmitt | C07C 213/06 560/217 |

OTHER PUBLICATIONS

International Preliminary Report on Patentability issued on PCT/US2014/016822, mailed Sep. 29, 2015.
International Search Report issued on PCT/US2014/016822, mailed Jun. 4, 2014.
Nelson Marans et al., "Nitroalkyl Esters of Acrylic, Crotonic and Methacrylic Acids 1", Journal of the American Chemical Society, vol. 72, No. 5, May 1, 1950, pp. 2125-2126.

* cited by examiner

*Primary Examiner* — Patrick Lewis
(74) *Attorney, Agent, or Firm* — Foley & Lardner LLP; Melissa El Menaouar; Joseph P. Meara

(57) ABSTRACT

Provided is a process for making (2-nitro)alkyl (meth) acrylate compounds of formula I: wherein n, R, $R^1$, $R^2$, $R^3$, $R^4$, $R^6$, $R^7$, and n are as defined herein, by a transesterification reaction between a nitroalcohol compound and a (meth)acrylate compound in the presence of a transesterification catalyst and a free radical inhibitor.

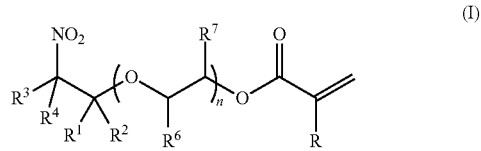

18 Claims, No Drawings

SYNTHESIS OF (2-NITRO)ALKYL (METH)ACRYLATES VIA TRANSESTERIFICATION OF (METH)ACRYLATE ESTERS

CROSS-REFERENCE TO RELATED APPLICATIONS

This applications is a 371 National Phase Application of PCT/US2014/016822, filed Feb. 18, 2014, which claims priority from U.S. provisional application Ser. No. 61/805,975, filed Mar. 28, 2013, which are incorporated herein by reference in their entireties.

FIELD

This invention relates generally to a process for making (2-nitro)alkyl (meth)acrylate compounds. More specifically, the process involves transesterification between methyl (meth)acrylate esters and nitroalcohol compounds.

BACKGROUND

Synthesis of (2-nitro)alkyl (meth)acrylates has been described in both patent and journal literature (e.g., U.S. Pat. Nos. 2,449,804, 2,388,844 and *J. Appl. Polym. Sci.* 1968, 12, 1683-1695). Typical procedures involve either (A) direct esterification of (meth)acrylic acid with 2-nitro alcohol in the presence of a mineral or organic acid catalyst in a hydrocarbon solvent that forms an azeotrope with the byproduct water; or (B) esterification reaction of acid chloride of (meth)acrylic acid with 2-nitro alcohol.

Both methods present disadvantages in a commercial scale synthesis of these materials. For example, for direct esterification the strong acid catalyst is removed through some type of wash or ion exchange resin treatment method, thus creating unwanted waste streams. Strong acid catalysts must be removed otherwise they can cause corrosion and can interfere with the applications of the product, for instance in corresponding polymer coatings. In addition, the strong acid catalysts can promote formation of oligomers and alcohol addition products of (meth)acrylic acid that are formed due to Michael addition side reactions. These side reactions often lead to yield loss. Likewise, esterification of acid chlorides requires the disposal of equimolar amounts of chloride salt by-products formed as the result of this chemistry. In addition, acid chloride raw material is not a commercial raw material for commodity applications. Although acid chloride raw material can be manufactured by reacting (meth)acrylic acid with thionyl chloride or phosgene, these reagents are highly toxic and require special handling. This reaction also leads to the formation of more unwanted side products such as sulfur dioxide and hydrochloric acid.

The problem addressed by this invention is the provision of a new process for making (2-nitro)alkyl (meth)acrylates.

STATEMENT OF INVENTION

We have now found that (2-nitro)alkyl (meth)acrylates of the formula I as described herein may be readily prepared in a process that is facile, commercially viable, and atom efficient. Advantageously compounds prepared by the invention find use in various applications. For instance, they may be incorporated into polymer backbones for use in paints and coatings.

Accordingly, there is provided a process for making a compound of formula I:

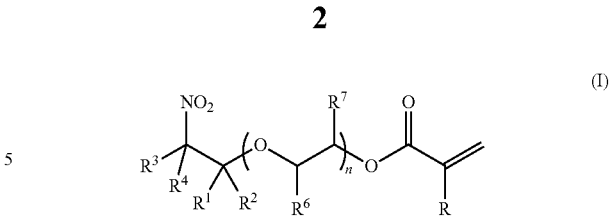

wherein n is from 0 to 100, R is H or $CH_3$; $R^1$ and $R^2$ are independently H, linear or branched $C_1$-$C_8$ alkyl optionally substituted with $NO_2$, or $R^1$ and $R^2$ together with the carbon atom to which they are attached form $C_3$-$C_{12}$ cycloalkyl; $R^3$ and $R^4$ are independently H, linear or branched $C_1$-$C_8$ alkyl, or a group of formula $C(R^1)(R^2)$—O—$R^5$, wherein $R^5$ is H or $C(=O)$—$C(R)=CH_2$, or $R^3$ and $R^4$, together with the carbon atom to which they are attached, form $C_3$-$C_{12}$ cycloalkyl; and $R^6$ and $R^7$ when present are independently H or $CH_3$, the process comprising: transesterifying a nitroalcohol compound of formula II:

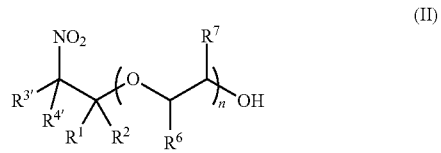

wherein $R^1$, $R^2$, $R^6$, $R^7$, and n are the same as in formula I; and $R^{3'}$ and $R^{4'}$ independently H, linear or branched $C_1$-$C_8$ alkyl, or a group of formula $C(R^1)(R^2)$—O—H, or $R^{3'}$ and $R^{4'}$, together with the carbon atom to which they are attached, form $C_3$-$C_{12}$ cycloalkyl, with a (meth)acrylate of formula III:

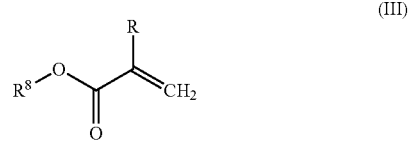

wherein R is the same as in formula I; and $R^8$ is linear or branched $C_1$-$C_8$ alkyl, in the presence of a transesterification catalyst and a free radical inhibitor, to form the compound of formula I, wherein: the transesterification catalyst is a basic catalyst, an organometallic catalyst, or mixtures thereof, and wherein the transesterification is conducted at a temperature of from 70 to 125° C. and a pressure of 400 mm Hg to 760 mm Hg.

DETAILED DESCRIPTION

Unless otherwise indicated, numeric ranges, for instance as in "from 2 to 10," are inclusive of the numbers defining the range (e.g., 2 and 10).

Unless otherwise indicated, ratios, percentages, parts, and the like are by weight.

"Alkyl," as used in this specification encompasses straight and branched chain aliphatic groups having the indicated number of carbon atoms. Preferred alkyl groups include, without limitation, methyl, ethyl, propyl, isopropyl, butyl, isobutyl, sec-butyl, tert-butyl, pentyl, and hexyl. The term "cycloalkyl" refers to saturated and partially unsaturated cyclic hydrocarbon groups having the indicated number of ring carbon atoms. Preferred cycloalkyl groups include, without limitation, cyclopropyl, cyclobutyl, cyclopentyl, cyclopentenyl, cyclohexyl, cyclohexenyl, cycloheptyl, and cyclooctyl. Cycloalkyl may be substituted, for instance with linear or branched $C_1$-$C_6$ alkyl.

"(Meth)acrylate" as used herein means acrylate, methacrylate, and mixtures thereof and the term "(meth)acrylic" means acrylic, methacrylic, and mixtures thereof.

As noted above, the invention provides a process for making (2-nitro)alkyl (meth)acrylate compounds of formula I:

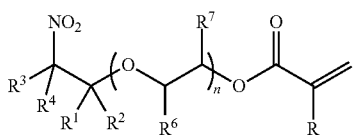

wherein n, R, $R^1$, $R^2$, $R^3$, $R^4$, $R^6$, $R^7$, and n are as defined above. The process employs a basic or organometallic (or mixtures thereof) catalyst for the transesterification of a nitroalcohol compound with a methacrylate to form the compounds of formula I.

Discovery of the ability of basic catalysts to provide a clean route for the synthesis of the formula I compounds according to the invention was surprising because nitroalcohol compounds, the precursors to formula I, are generally expected to decompose readily under basic conditions, especially when temperatures are greater than 100° C. It was unexpected, therefore, that basic catalysts lead to a clean transesterification reaction.

Transesterification by the process of the invention provides several advantages, including: (meth)acrylate esters as defined by structure III are commercially available commodity raw materials and are easily recycled reactants; the inventive process typically has few or no side reactions and leads to favorable product yield; catalysts used in the process can typically be left in the product or recycled.

According to the process of the invention, a nitroalcohol compound of formula II:

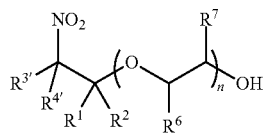

wherein $R^1$, $R^2$, $R^6$, $R^7$, and n are the same as in formula I; and $R^{3'}$ and $R^{4'}$ independently H, linear or branched $C_1$-$C_8$ alkyl, or a group of formula $C(R^1)(R^2)$—O—H, or $R^{3'}$ and $R^{4'}$, together with the carbon atom to which they are attached, form $C_3$-$C_{12}$ cycloalkyl, is esterified, in the presence of a transesterification catalyst and a free radical inhibitor, with a (meth)acrylate of formula III:

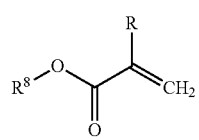

wherein R is the same as in formula I; and $R^8$ is linear or branched $C_1$-$C_8$ alkyl.

In some embodiments of the invention, $R^1$ in the nitroalcohol compound of formula II (and in the corresponding (2-nitro)alkyl (meth)acrylate compounds of formula I) is H and $R^2$ is H or linear or branched $C_1$-$C_8$ alkyl optionally substituted with $NO_2$. Preferred alkyl in this embodiment include linear or branched $C_1$-$C_6$ alkyl, alternatively $C_1$-$C_4$ alkyl, optionally substituted with $NO_2$. In some embodiments, both $R^1$ and $R^2$ are H.

In some embodiments, $R^1$ and $R^2$ are independently linear or branched $C_1$-$C_8$ alkyl optionally substituted with $NO_2$, or $R^1$ and $R^2$ together with the carbon atom to which they are attached form $C_3$-$C_{12}$ cycloalkyl. Preferred alkyl in this embodiment include linear or branched $C_1$-$C_6$ alkyl, alternatively $C_1$-$C_4$ alkyl, optionally substituted with $NO_2$. Preferred cycloalkyl include $C_3$-$C_{12}$ cycloalkyl, more preferably cyclopentyl, cyclohexyl, cycloheptyl, or cyclooctyl. Cyclohexyl is preferred.

In some embodiments, $R^3$ is H and $R^4$ is H, linear or branched $C_1$-$C_8$ alkyl, or a group of formula $C(R^1)(R^2)$—O—$R^5$. Preferred alkyl in this embodiment include linear or branched $C_1$-$C_6$ alkyl, alternatively $C_1$-$C_4$ alkyl, alternatively methyl or ethyl. Preferably, $R^1$ and $R^2$ and are both H in this embodiment.

In some embodiments, $R^3$ and $R^4$ are independently linear or branched $C_1$-$C_8$ alkyl, or $R^3$ and $R^4$, together with the carbon atom to which they are attached, form $C_3$-$C_{12}$ cycloalkyl. Preferred alkyl in this embodiment include linear or branched $C_1$-$C_6$ alkyl, alternatively $C_1$-$C_4$ alkyl, or more specifically methyl, ethyl, or propyl. Preferred cycloalkyl include $C_3$-$C_{12}$ cycloalkyl, more preferably cyclopentyl, cyclohexyl, cycloheptyl, or cyclooctyl. Cyclohexyl is preferred.

In some embodiments, $R^3$ and $R^4$ are independently a group of formula $C(R^1)(R^2)$—O—$R^5$. In this embodiment, it may be preferred for one or both of the $R^5$ groups to be H. It may also be preferred for both $R^5$ groups to be $C(=O)$—$C(R)=CH_2$ (where R is H or $CH_3$).

In some embodiments, R is H. In some embodiments, R is $CH_3$.

In some embodiments, one of $R^6$ and $R^7$ is H and the other is H or $CH^3$.

Formula II (and I) includes the variable "n." This variable represents the optional presence of an ethylene oxide or propylene oxide moiety in the formula II or formula I compound and therefore, when greater than zero, represents an average degree of ethoxylation or propoxylation. It is determined from the amount of ethylene oxide or propylene oxide starting materials used in the synthesis of the formula II compound. Ethoxylation and propoxylation of an alcohol using ethylene oxide or propylene oxide is a well-known technique that may be carried out by a person of ordinary skill in the art using established literature methods.

In some embodiments of the invention, n is zero.

In some embodiments, n is from 0 to 100, alternatively from 0 to 50, alternatively from 0 to 20, or alternatively from 0 to 10.

Preferred compounds of formula II include: 2-nitro-2-methyl-l-propanol, 2-nitrobutanol, 2-methyl-2-nitropropane-1,3-diol, 2-ethyl-2-nitropropane-1,3-diol, 2-(hydroxymethyl)-2-nitropropane-1,3-diol, 3-nitrooctan-4-ol, 2-methyl-2-nitrobutanol, (1-nitrocyclohexyl)methanol, 1-(nitromethyl)cyclohexanol, and 2,5,6-trimethyl-2,6-dinitroheptan-3-ol.

In some embodiments, $R^8$ in the formula III compounds is $C_1$-$C_3$ alkyl, alternatively it is ethyl, or alternatively it is methyl. Preferred compounds of formula 7 include methyl acrylate and methyl methacrylate.

The transesterification catalyst for use in the process is a basic catalyst, an organometallic catalyst, or a mixture thereof. Typically, the catalyst is present at a concentration of 0.1 to 10 mole percent, preferably 0.5 to 5 mole percent, based on the nitroalcohol compound.

In some embodiments of the invention, the transesterification catalyst is dibutyltin oxide, a zirconium complex, a hafnium complex, a tetra-alkoxy titanate (e.g. titanium(IV) tetra-butoxide, titanium(IV) tetra-isopropoxide, titanium (IV) tetra-2-ethylhexyloxide), lithium hydroxide, barium oxide, magnesium oxide, strontium oxide, calcium oxide, magnesium methylate, 1,4-diazabicyclo[2.2.2]octane, a basic ion exchange resin, or a mixture of two or more thereof.

In some embodiments of the invention, the transesterification catalyst is a tetra-alkoxy titanate (e.g. titanium(IV) tetra-butoxide, titanium(IV) tetra-isopropoxide, titanium (IV) tetra-2-ethylhexyloxide), barium oxide, magnesium oxide, strontium oxide, calcium oxide, magnesium methylate, a basic ion exchange resin, or a mixture of two or more thereof.

In some embodiments, the transesterification catalyst is dibutyltin oxide, a zirconium complex, a hafnium complex, 1,4-diazabicyclo[2.2.2]octane, or a mixture of two or more thereof.

In some embodiments, the transesterification catalyst is a zirconium complex. In some embodiments, the transesterification catalyst is zirconium acetyl acetonate.

A free radical inhibitor is included in the process of the invention in order to minimize polymerization of reactants. In some embodiments, examples of suitable free-radical inhibitors include, without limitation, phenothiazine, hydroquinone, methyl ether of hydroquinone, 4-Hydroxy-TEMPO, or mixtures thereof. The free radical inhibitor may be present, for instance, at a concentration of 10 to 10,000 parts per million, preferably 100 to 1000 parts per million, based on the nitroalcohol compound.

In a typical procedure for carrying out the process of the invention, the (meth)acrylate compound is transesterified with the nitroalcohol compound, in the presence of a transesterification catalyst and the free radical inhibitor, by heating the mixture at elevated temperature, such as from 70 to 125° C., preferably from 90 to 100° C. The reaction may be conducted at atmospheric pressure, or at reduced pressure. For instance, a range of 400 mm Hg to 760 mm Hg may be suitable. Optionally, the reactants are dissolved or dispersed in a solvent. Toluene is a desirable solvent, although other solvents may be substituted. The reaction is continued until a desired amount of product is formed, for instance 1 to 12 hours.

Typically, the mole ratio of (meth)acrylate compound to nitroalcohol in the invention may be from 1:1 to 20:1. In some embodiments, it is preferred that an excess of the (meth)acrylate, such as from 1.5 to 10 molar excess, be used in the process. The residual (meth)acrylate can then be recycled. In some embodiments, it may be advantageous to employ a distillation column in order to establish an azeotrope between the (meth)acrylate and alcohol byproduct. This azeotrope effectively removes the alcohol byproduct which drives the transester equilibrium reaction forward.

It is also desirable to dry the starting materials prior to the esterification reaction. Drying may be accomplished by various methods known to those skilled in the art, including for instance, by distilling off a portion of, for example, the (meth)acrylate or the solvent. A target water level of less than 0.01 weight percent is preferred.

The process of the invention results in the clean formation of (2-nitro)alkyl (meth)acrylate compounds of formula I:

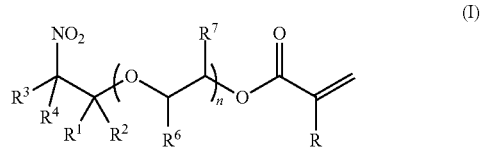

wherein n, R, $R^1$, $R^2$, $R^3$, $R^4$, $R^6$, $R^7$, and n are as defined above.

Compounds of formula I may be used for a variety of purposes. For instance, they may be employed as monomers in the preparation of polymer binders for architectural paints or coatings.

Non-limiting examples of compounds of formula I are shown in Table 1. In some embodiments, the monomer unit of formula I is as shown in Table 1.

TABLE 1

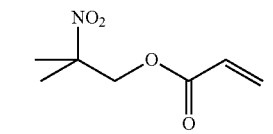

2-nitro-2-methylpropyl acrylate

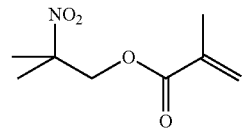

2-nitro-2-methylpropyl methacrylate

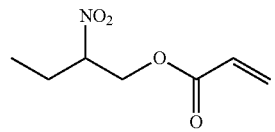

2-nitrobutyl acrylate

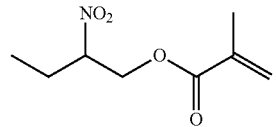

2-nitrobutyl methacrylate

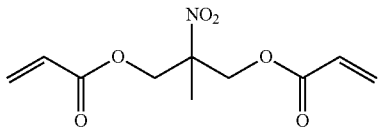 [SMILES: C=CC(=O)OCC(C)(COC(=O)C=C)[N+](=O)[O-]]

2-methyl-2-nitropropane-1,3-diyl diacrylate

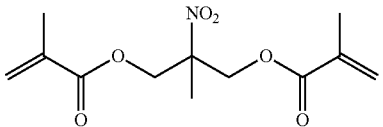 [SMILES: C=C(C)C(=O)OCC(C)(COC(=O)C(=C)C)[N+](=O)[O-]]

TABLE 1-continued 2-methyl-2-nitropropane-1,3-diyl bis(2-methylacrylate)

3-hydroxy-2-methyl-2-nitropropyl acrylate 3-hydroxy-2-methyl-2-nitropropyl methacrylate 2-ethyl-2-nitropropane-1,3-diyl diacrylate 2-ethyl-2-nitropropane-1,3-diyl bis(2-methylacrylate)

2-(hydroxymethyl)-2-nitrobutyl acrylate 2-(hydroxymethyl)-2-nitrobutyl methacrylate 3-hydroxy-2-(hydroxymethyl)-2-nitropropyl acrylate TABLE 1-continued 3-hydroxy-2-(hydroxymethyl)-2-nitropropyl methacrylate 2-(hydroxymethyl)-2-nitropropane-1,3-diyl diacrylate 2-(hydroxymethyl)-2-nitropropane-1,3-diyl bis(2-methylacrylate)

3-nitrooctan-4-yl acrylate 3-nitrooctan-4-yl methacrylate

TABLE 1-continued

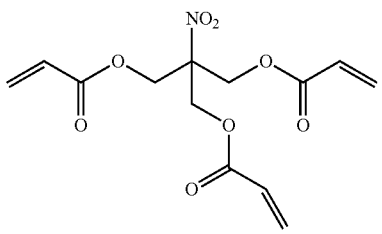 [SMILES: C=CC(=O)OCC(COC(=O)C=C)(COC(=O)C=C)[N+](=O)[O-]]

2-((acryloyloxy)methyl)-2-nitropropane-1,3-diyl diacrylate

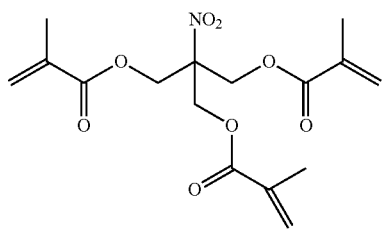 [SMILES: C=C(C)C(=O)OCC(COC(=O)C(=C)C)(COC(=O)C(=C)C)[N+](=O)[O-]]

2-((methacryloyloxy)methyl)-2-nitropropane-1,3-diyl bis(2-methylacrylate)

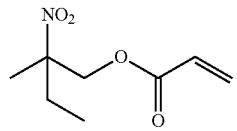

2-methyl-2-nitrobutyl acrylate

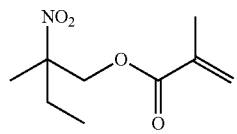

2-methyl-2-nitrobutyl methacrylate

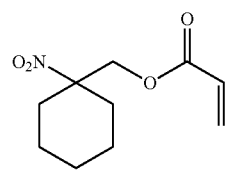

(1-nitrocyclohexyl)methyl acrylate

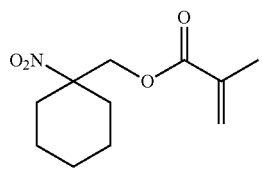 [SMILES: C=C(C)C(=O)OCC1([N+](=O)[O-])CCCCC1]

(1-nitrocyclohexyl)methyl methacrylate

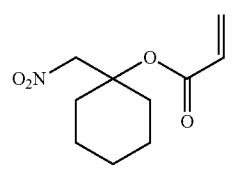

1-(nitromethyl)cyclohexyl acrylate

TABLE 1-continued

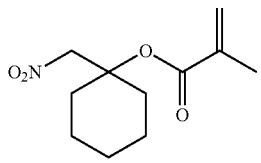 [SMILES: C=C(C)C(=O)OC1(C[N+](=O)[O-])CCCCC1]

1-(nitromethyl)cyclohexyl methacrylate

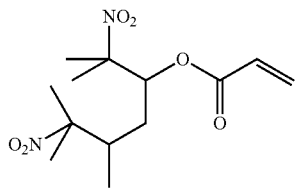 [SMILES: C=CC(=O)OC(CC(C)C(C)(C)[N+](=O)[O-])C(C)(C)[N+](=O)[O-]]

2,5,6-trimethyl-2,6-dinitroheptan-3-yl acrylate

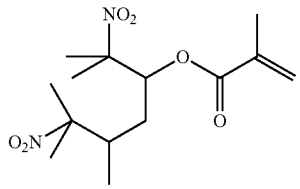 [SMILES: C=C(C)C(=O)OC(CC(C)C(C)(C)[N+](=O)[O-])C(C)(C)[N+](=O)[O-]]

2,5,6-trimethyl-2,6-dinitroheptan-3-yl methacrylate

Some embodiments of the invention will now be described in detail in the following Examples.

EXAMPLES

Example 1

Synthesis of 2-Nitro-2-Methylpropyl Methacrylate

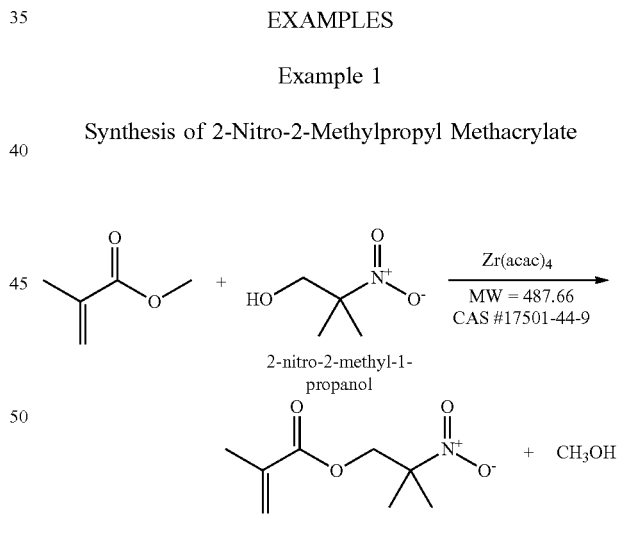

Procedure I: To a 1000 ml 4 necked flask fitted with a stirrer, thermometer, 10-tray distillation head and a reflux splitter was added 2-nitro-2 methyl propanol (123.5 g, 1.04 mol) and toluene (350 ml). The resulting mixture was heated to 100° C. under reduced pressure (400 mmHg) and approximately 30 ml of distillate was collected in the receiver in order to dry the contents of the flask via an azeotrope formed between water and the solvent. Then heating turned off and the pot solution was allowed to cool 50-60° C. To the solution were added phenothiazine (115 mg), methyl methacrylate, MMA, (119 g, 1.2 mol) and zirconium acetyl acetonate (7.25 g, 0.015 mol). The reaction mixture was heated to 120° C. under reduced pressure (700 mmHg). Reflux/distillation splitter was set at 20/5 and the distillate was collected when the vapor temperature was between 65-70° C. over a 4.5 hour period, weighed accurately and analyzed by quantitative $^1$H-NMR. The amount MeOH byproduct formed was calculated from this analysis and it revealed approximately 75% of starting nitro alcohol was converted. It also indicated that approximately 21 g of MMA was lost to the distillate. To the reaction was added MMA (20 g, 0.2 mol) and more zirconium acetyl acetonate (2.25 g, 0.005 mol). Heating continued for at 120° C. another 4 hrs during which approximately 58 g of distillated was collected and $^1$H-NMR analysis of reaction mixture revealed 87% conversion of nitro alcohol. To the reaction mixture was added MMA (26 g, 0.26 mol) and zirconium acetyl acetonate (2 g, 0.004 mol). Heating continued for another 2 hrs after which toluene and unreacted excess MMA were removed in a rotary evaporator to yield 184.5 g. The crude product showed greater than 80% purity by $^1$H-NMR. Major impurities were toluene (7%), unreacted alcohol starting material (10%) and MMA (2%). Product yield was 77%.

Procedure II: To a 1000 ml 4 necked flask fitted with a stirrer, thermometer, 10-tray distillation head and a reflux splitter was added 2-nitro-2-methyl propanol (119 g, 1 mol) phenothiazine (70 mg) and MMA (350 ml). The resulting mixture was heated to 100° C. under reduced pressure (400 mmHg). Heating turned off after 50 ml of MMA was collected and the pot solution was allowed to cool to 50-60° C. To the solution was added zirconium acetyl acetonate (7.25 g, 0.015 mol). The resulting solution was heated to 100° C. and the distillate was collected at reduced pressure 495 mmHg After 6 hrs of reaction time distillation vapor temperature began to fall from the peak temperature of 70° C.

Approximately 150 g of distillate was collected and 1H-NMR analysis of the pot revealed 89% conversion of starting nitro alcohol. To the reaction was added MMA (25 g, 0.25 mol) and zirconium acetyl acetonate (0.25 g, 0.5 mmol). Heating continued for another 2 hrs and $^1$H-NMR analysis of reaction mixture revealed no changes of nitro alcohol. Excess MMA and unreacted nitro alcohol starting material were removed by vacuum distillation (Pot temp. 93° C., vapor Temp. 82-87° C., pressure 3 mmHg), to give >95% pure monomer, weighing 150 g, with an overall yield of 75%.

Example 2

Synthesis of 2-Methyl-2-Nitropropane-1,3-Diyl Bis(2-Methylacrylate) (Prophetic)

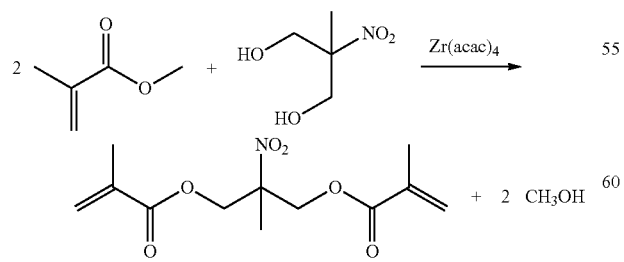

2-Methyl-2-nitropropane-1,3-diyl bis(2-methylacrylate) may be prepared using essentially the same procedures as described in Example 1 except for substituting 2-methyl-2-nitropropane-1,3-diol as the starting nitroalcohol compound, doubling the number of equivalents of methyl methacrylate, and making other non-critical modifications as needed.

Example 3

Synthesis of 2-(Methacryloyloxy)methyl)-2-Nitropropane-1,3-Diyl Bis(2-Methylacrylate) (Prophetic)

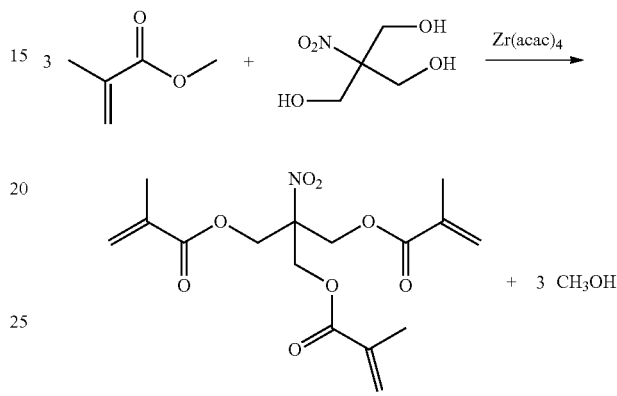

2-(Methacryloyloxy)methyl)-2-nitropropane-1,3-diyl bis (2-methylacrylate) may be prepared using essentially the same procedures as described in Example 1 except for substituting 2-(hydroxymethyl)-2-nitropropane-1,3-diol as the starting nitroalcohol compound, tripling the number of equivalents of methyl methacrylate, and making other non-critical modifications as needed.

Example 4

Synthesis of (1-Nitrocyclohexyl)methyl Methacrylate (Prophetic)

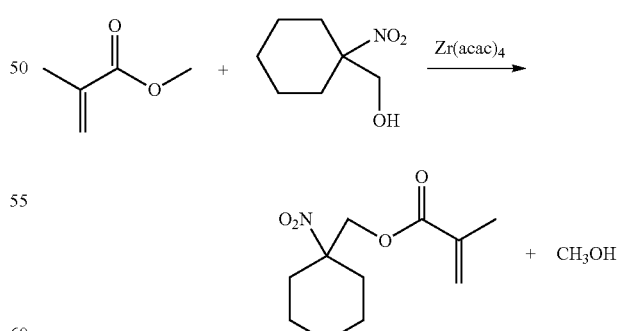

(1-Nitrocyclohexyl)methyl methacrylate may be prepared using essentially the same procedures as described in Example 1 except for substituting (1-nitrocyclohexyl) methanol as the starting nitroalcohol compound and making non-critical modifications as needed.

What is claimed is:

1. A process for making a compound of formula I:

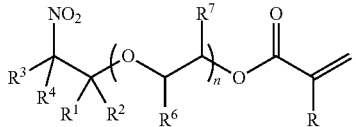

wherein n is from 0 to 100;
R is H or $CH_3$;
$R^1$ and $R^2$ are independently H, linear or branched $C_1$-$C_8$ alkyl optionally substituted with $NO_2$, or $R^1 R^2$ together with the carbon atom to which they are attached form $C_3$-$C_{12}$ cycloalkyl;
$R^3$ and $R^4$ are independently H, linear or branched $C_1$-$C_8$ alkyl, or a group of formula $C(R^1)(R^2)$—O—$R^5$, wherein $R^5$ is H or C(=O)—C(R)=$CH_2$, or $R^3$ and $R^4$, together with the carbon atom to which they are attached, form $C_3$-$C_{12}$ cycloalkyl; and
$R^6$ and $R^7$ when present are independently H or $CH_3$, the process comprising:
transesterifying a nitroalcohol compound of formula II:

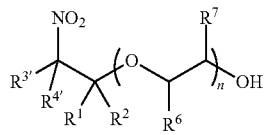

wherein $R^1$, $R^2$, $R^6$, $R^7$, and n are the same as in formula I; and
$R^{3'}$ and $R^{4'}$ are independently H, linear or branched $C_1$-$C_8$ alkyl, or a group of formula $C(R^1)(R^2)$—O—H, or $R^{3'}$ and $R^{4'}$, together with the carbon atom to which they are attached, form $C_3$-$C_{12}$ cycloalkyl,
with a (meth)acrylate of formula III:

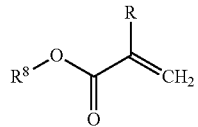

wherein R is the same as in formula I; and
$R^8$ is linear or branched $C_1$-$C_8$ alkyl,
in the presence of a transesterification catalyst and a free radical inhibitor to form the compound of formula I, wherein the transesterification catalyst is a basic catalyst, a zirconium complex, a hafnium complex, or mixtures thereof, and wherein the transesterification is conducted at a temperature of from 70 to 125 ° C. and a pressure of 400 mm Hg to 760 mm Hg.

2. The process of claim 1 wherein the transesterification catalyst is a zirconium complex, a hafnium complex, or a mixture thereof.

3. The process of claim 1 wherein the transesterification catalyst is a hafnium complex.

4. The process of claim 1 wherein the transesterification catalyst is a zirconium complex.

5. The process of claim 1 wherein the mole ratio of (meth)acrylate compound to nitroalcohol is from 1:1 to 20:1.

6. The process of claim 1 wherein excess (meth)acrylate and its corresponding alcohol form an azeotropic mixture and wherein this byproduct alcohol is removed by azeotropic distillation.

7. The process of claim 1 wherein the free-radical inhibitor is, phenothiazine, hydroquinone, methyl ether of hydroquinone, 4-Hydroxy-TEMPO, or mixtures thereof.

8. The process of claim 1 wherein $R^1$ is H and $R^2$ is H or linear or branched $C_1$-$C_8$ alkyl optionally substituted with $NO_2$.

9. The process of claim 1 wherein $R^{3'}$ and $R^{4'}$ are independently linear or branched $C_1$-$C_8$ alkyl, or $R^{3'}$ and $R^{4'}$, together with the carbon atom to which they are attached, form $C_3$-$C_{12}$ cycloalkyl.

10. The process of claim 1 wherein the compound of formula I is: 2-methyl-2-nitropropyl acrylate; 2-methyl-2-nitropropyl methacrylate; 2-nitrobutyl acrylate; 2-nitrobutyl methacrylate; 2-methyl-2-nitropropane-1,3-diyl diacrylate; 2-methyl-2-nitropropane-1,3-diyl bis(2-methylacrylate); 3-hydroxy-2-methyl-2-nitropropyl acrylate; 3-hydroxy-2-methyl-2-nitropropyl methacrylate; 2-ethyl-2-nitropropane-1,3-diyl diacrylate; 2-ethyl-2-nitropropane-1,3-diyl bis(2-methylacrylate); 2-(hydroxymethyl)-2-nitrobutyl acrylate; 2(hydroxymethyl)-2-nitrobutyl methacrylate; 3-hydroxy-2-(hydroxymethyl)-2-nitropropyl acrylate; 3-hydroxy-2-(hydroxymethyl)-2-nitropropyl methacrylate; 2-(hydroxymethyl)-2-nitropropane-1,3-diyl diacrylate; 2-(hydroxymethyl)-2-nitropropane-1,3-diyl bis(2methylacrylate); 3-nitrooctan-4-yl acrylate; 3-nitrooctan-4-yl methacrylate; 2-((acryloyloxy)methyl)-2-nitropropane-1,3-diyl diacrylate; 2-((methacryloyloxy)methyl)-2-nitropropane-1,3-diyl bis(2-methylacrylate); 2-methyl-2-nitrobutyl acrylate; 2-methyl-2-nitrobutyl methacrylate; (1-nitrocyclohexyl)methyl acrylate; (1-nitrocyclohexyl)methyl methacrylate; 1-(nitromethyl)cyclohexyl acrylate; 1-(nitromethyl)cyclohexyl methacrylate; 2,5,6-trimethyl-2,6-dinitroheptan-3-yl acrylate; or 2,5,6-trimethyl-2,6-dinitroheptan-3-yl methacrylate, or an alkoxylated derivative thereof.

11. The process of claim 1 wherein $R^1$ is H and $R^2$ is H or linear or branched $C_1$-$C_6$ alkyl optionally substituted with $NO_2$.

12. The process of claim 1 wherein $R^1$ is H and $R^2$ is H.

13. The process of claim 1 wherein $R^1$ and $R^2$ together with the carbon atom to which they are attached, form a cyclohexyl group.

14. The process of claim 1 wherein $R^{3'}$ and $R^{4'}$ together with the carbon atom to which they are attached, form a cyclohexyl group.

15. The process of claim 4 wherein $R^1$ is H and $R^2$ is H or $R^1$ and $R^2$ together with the carbon atom to which they are attached, form a cyclohexyl group;
the transesterification catalyst is present at a concentration of 0.1 to 10 mol %.; and
n is 0.

16. The process of claim 1 wherein the transesterification catalyst is zirconium acetyl acetonate.

17. The process of claim 1 wherein the transesterification catalyst is a basic catalyst.

18. The process of claim 17 wherein the transesterification catalyst is lithium hydroxide.

* * * * *